(12) United States Patent
Gupta et al.

(10) Patent No.: US 11,103,157 B2
(45) Date of Patent: Aug. 31, 2021

(54) BREATH GAS ANALYSIS

(71) Applicant: CEDARS-SINAI MEDICAL CENTER, Los Angeles, CA (US)

(72) Inventors: Kapil Gupta, Los Angeles, CA (US); Mark Pimentel, Los Angeles, CA (US); Ali Rezaie, West Hollywood, CA (US)

(*) Notice: Subject to any disclaimer, the term of this patent is extended or adjusted under 35 U.S.C. 154(b) by 563 days.

(21) Appl. No.: 15/757,139

(22) PCT Filed: Aug. 30, 2016

(86) PCT No.: PCT/US2016/049528
§ 371 (c)(1),
(2) Date: Mar. 2, 2018

(87) PCT Pub. No.: WO2017/040546
PCT Pub. Date: Mar. 9, 2017

(65) Prior Publication Data
US 2018/0271404 A1 Sep. 27, 2018

Related U.S. Application Data

(60) Provisional application No. 62/213,517, filed on Sep. 2, 2015.

(51) Int. Cl.
*A61B 5/08* (2006.01)
*G01N 33/497* (2006.01)
(Continued)

(52) U.S. Cl.
CPC ............. *A61B 5/082* (2013.01); *A61B 5/097* (2013.01); *G01N 5/02* (2013.01); *G01N 33/497* (2013.01)

(58) Field of Classification Search
None
See application file for complete search history.

(56) References Cited

U.S. PATENT DOCUMENTS 5,291,898 A   3/1994  Wolf
6,364,938 B1  4/2002  Birbara et al.
(Continued)

FOREIGN PATENT DOCUMENTS

AU    2016315721 A1   3/2018
BR    11-2018-004097 A2  4/2018
(Continued)

OTHER PUBLICATIONS

Ghoshal; How to Interpret Hydrogen Breath Tests; J Neurogastroenterol Motil, vol. 17 No. Jul. 3, 2011 (Year: 2011).*
(Continued)

*Primary Examiner* — Kaylee R Wilson
*Assistant Examiner* — Jay B Shah
(74) *Attorney, Agent, or Firm* — Nixon Peabody LLP

(57) ABSTRACT

Systems and methods have been developed for implementation of a portable SIBO testing system for convenient sampling of intestinal gases exhaled from a patient's breath. These devices may be in the form of a hand held meter that would integrate with a smartphone or other device with an application that can record data relating to food consumed by a user. Various technologies may be utilized to measure the levels of gases exhaled by a user, which may include (1) sorbent based technology and (2) membrane based technology. In some examples, the system will determine an indication of whether a patient has SIBO by adjusting a change in exhaled hydrogen concentration by a methane level exhaled by a patient.

10 Claims, 10 Drawing Sheets

(51) Int. Cl.
*A61B 5/097* (2006.01)
*G01N 5/02* (2006.01)

(56) References Cited

U.S. PATENT DOCUMENTS

| | | | |
|---|---|---|---|
| 7,048,906 | B2 | 5/2006 | Lin et al. |
| 7,288,136 | B1 | 10/2007 | Gray et al. |
| 7,736,622 | B2 | 6/2010 | Lin et al. |
| 8,383,026 | B1 | 3/2013 | Leubke et al. |
| 8,500,854 | B1 | 8/2013 | Pennline et al. |
| 8,821,614 | B1 | 9/2014 | Albenze et al. |
| 9,050,579 | B1 | 6/2015 | Wickramanayake et al. |
| 9,186,854 | B1 | 11/2015 | Luebke et al. |
| 2004/0147038 | A1 | 7/2004 | Lewis et al. |
| 2006/0074335 | A1 | 4/2006 | Ben-Oren et al. |
| 2006/0182693 | A1 | 8/2006 | Kristiansen et al. |
| 2006/0246045 | A1* | 11/2006 | Pimentel .............. A61K 36/064 424/93.45 |
| 2008/0045825 | A1 | 2/2008 | Melker et al. |
| 2008/0182291 | A1 | 7/2008 | Pimentel |
| 2010/0209507 | A1 | 8/2010 | Lin et al. |
| 2011/0023581 | A1 | 2/2011 | Wolf |
| 2012/0150056 | A1 | 6/2012 | Christman et al. |
| 2012/0234076 | A1 | 9/2012 | Rigas |
| 2012/0285320 | A1 | 11/2012 | Heald et al. |
| 2014/0206636 | A1 | 7/2014 | Lin et al. |

FOREIGN PATENT DOCUMENTS

| | | | |
|---|---|---|---|
| CA | 2996425 | A1 | 3/2017 |
| CL | 2018570 | | 6/2018 |
| CN | 101650351 | A | 2/2010 |
| EP | 2267445 | A1 | 12/2010 |
| EP | 3344995 | A1 | 7/2018 |
| IN | 201827007178 | A | 2/2018 |
| KR | 20180043832 | A | 4/2018 |
| MX | 20180002721 | A | 4/2018 |
| WO | 2002083926 | A2 | 10/2002 |
| WO | 2017/040546 | A1 | 3/2017 |
| WO | 2018156937 | A1 | 8/2018 |

OTHER PUBLICATIONS

International Search Report and Written Opinion of PCT/US2018/019490, dated Apr. 30, 2018, 9 Pages.
Lusk et al., Hydrogen Sulfide Monitoring Near Oil and Gas Production Facilities in Southeastern New Mexico and Potential Effects of Hydrogen Sulfide to Migratory Birds and Other Wildlife, 2010, U.S. Department of the Interior Fish & Wildlife Service Environmental Contaminants Program, 102 Pages.
Weaver et al., Incidence of Methanogenic Bacteria in a Sigmoidoscopy Population: an Association of Methanogenic Bacteria and Diverticulosis, 1986, Gut, vol. 27, pp. 698-704.
Supplementary Search Report of SG 11201801664P, dated Jan. 17, 2020, 3 pages.
Cloarec et al., Breath hydrogen response to lactulose in healthy subjects: relationship to methane producing status. Gut, Mar. 1, 1990, vol. 31, No. 3, pp. 300-304.
Cowie et al., Membrane Inlet Ion Trap Mass Spectrometry for the Direct Measurement of Dissolved Gases in Ecological Samples, Journal of Microbiological Methods, 1999, vol. 35(1), pp. 1-12.
Lazik, D., Membrane Based Measurement Technology for in situ Monitoring of Gases in Soil, Sensors, 2009, vol. 9, pp. 756-767.
Saad et al., Breath Tests for Gastrointestinal Disease: The Real Deal or Just a Lot of Hot Air?, Gastroenterology, 2007, vol. 133, pp. 1763-1766.
Scarlata, K., The Complete Idiot's Guide to Eating Well with IBS, New York, NY, Penguin Group, 2010.
Wang et al., Measurement of Mercury in Flue Gas Based on an Aluminum Matrix Sorbent, The Scientific World Journal, 2011, vol. 11, pp. 2469-2479.
EP 16842833.2 Partial Search Report dated Jan. 30, 2019, 17 pages.
CL 201800570 Search Report and Written Opinion dated Apr. 12, 2019, 17 pages.
SG 11201801664P Search Report and Written Opinion dated Mar. 29, 2019, 10 pages.
EP 16842833.2 Supp Search Report dated Apr. 29, 2019, 16 pages.
ISR and WO PCT/US2016/049528 dated Feb. 1, 2017, 13 pages.
IPRP PCT/US2016/049528 dated Mar. 15, 2018, 2 pages.

* cited by examiner

BREATH GAS ANALYSIS

CROSS-REFERENCE TO RELATED APPLICATIONS

This application is a National Phase of International Application No. PCT/US2016/049528, filed Aug. 30, 2016, which designated the U.S. and that International Application was published under PCT Article 21(2) in English. This application claims priority under 35 U.S.C. § 119(e) to U.S. Provisional Application No. 62/213,517, filed Sep. 2, 2015, the contents of which are herein incorporated by reference in their entirety.

FIELD OF THE INVENTION

The present invention is directed to systems and methods for analyzing the gases exhaled in the breath of a patient.

BACKGROUND OF THE INVENTION

The following description includes information that may be useful in understanding the present invention. It is not an admission that any of the information provided herein is prior art or relevant to the presently claimed invention, or that any publication specifically or implicitly referenced is prior art.

The human gastro-intestinal system is home to billions of bacterial cells that typically aid in digestion, but can be harmful if they grow too prolifically. These bacteria feed on the foods ingested by humans and produce both useful and harmful by-products. Bacteria are usually thousands of times less prevalent in the small intestine than in the large intestine. However, in some patients experiencing small intestine bacterial overgrowth ("SIBO"), the number of bacteria in the small intestine increase to the point that they approach the quantities of the large intestine. SIBO causes excessive gas production which can create discomfort and uncomfortable symptoms in a patient. For instance, a patient with excessive gas production may experience abdominal pain, bloating, excessive burping, flatus, discomfort generally and nausea. SIBO is thought to affect a significant number (some 10%) of adults.

Research (such as that disclosed in U.S. Pat. No. 8,388,935) has drawn an extensive but imperfectly-defined relationships between SIBO and numerous conditions such as irritable bowel syndrome (IBS), fibromyalgia, chronic pelvic pain syndrome, depression, impaired mentation, halitosis, tinnitus, sugar craving, autism, attention deficit/hyperactivity disorder, drug sensitivity, an autoimmune disease, and Crohn's disease. Using the tools currently available, caregivers have been able to correlate SIBO with some of these conditions in certain patients. Unfortunately, however, each patient's bacterial landscape is fairly unique, and therefore, universal correlations are difficult, if not impossible, to achieve. Accordingly, single tests in a laboratory are rarely determinative for diagnostic purposes.

Concentrations of $H_2S$, $CH_4$ and $H_2$ exhaled in the breath have been shown in numerous clinical studies to be linked to SIBO, though it appears that every patient is affected somewhat differently. For instance, concentrations in the ranges of $H_2S$ (~0.01-10 ppm), $CH_4$ (~1-50 ppm) and $H_2$ (~1-50 ppm) have been shown to be clinically significant.

Furthermore, excessive methane production has been shown to be associated with obesity and excess gas production has been shown to be associated with irritable bowel syndrome. Recently, there has been a higher level of interest in SIBO due to its possible link with irritable bowel syndrome. Furthermore, higher levels of methane are indicative of SIBO that causes constipation.

One mechanism that can lead to SIBO and the production of excess gases is the malabsorption of sugars. Malabsorption of sugars can cause the above mentioned symptoms of excess gases which reduce the quality of life of sufferers. For instance, more than 50 million Americans cannot adequately digest lactose. This can lead to symptoms of non-ulcerative dyspepsia and irritable bowel syndrome, such as bloating, diarrhea, flatulence, abdominal cramps and severe discomfort. The malabsorption results in hydrogen and methane being produced in the digestive system—mainly by the bacterial fermentation of carbohydrates (sugars, starches and vegetable fibers). Although most of the gases generated remain in the gut, some of these gases dissolve into the blood stream through the intestinal wall. Then the gases may be transported to the lungs where they are exhaled in the breath.

Additionally, some of the increased amounts of gas created by the bacteria are passed as flatus. Malabsorption of sugars in the small intestine (where there are normally few bacteria) may result in their passage to the large intestine (where there are very high concentrations of bacteria). This results in increased bacterial numbers and gas production which can push bacteria back into the small intestine as the ileocecal valve becomes insufficient to cope with the increasing intracolic pressure. Bacteria in the small intestine, when present in large numbers, can compete with the human host for the food that is eaten. This can lead to vitamin and mineral deficiencies. In advanced cases of SIBO, the bacteria consume enough of the ingested food and nutrition that there are insufficient calories to be digested and absorbed by the patient, which could cause malnutrition.

The symptoms of fructose malabsorption (which may affect approx. 30% of the European population), for instance, are characterized by the inability to absorb fructose in the small intestine leading to bloating, cramps, osmotic diarrhea and other symptoms of irritable bowel syndrome which can be seen in about 50% of fructose malabsorbers. Low serum tryptophan and signs of folic acid and/or zinc deficiency can also be linked with the inability to absorb fructose efficiently.

Currently, SIBO is diagnosed using a predetermined diet regime prior to a lab test of the exhaled gases of the patient. For example, the patient may take a dose of carbohydrate such as lactulose (typically 10 g) or glucose (typically 50 g). Then, after ingestion, samples of the patient's breath are analyzed for hydrogen, typically every 15-20 minutes for up to 3 hours. Where the patient is administered glucose a rise in hydrogen concentration, typically >10 ppm (parts per million) above the baseline level is indicative of a positive test.

Lactulose is a sugar that is digested by colonic bacteria and not by the human host. The ingested lactulose should pass through the small intestine undigested and reach the colon where the bacteria produce gas. In the normal individual, there is a single peak of gas in the breath following the ingestion of lactulose when the lactulose enters the colon. Individuals with SIBO may produce two significant peaks of gas in the breath. The first abnormal peak occurs as the lactulose passes the gas-producing bacteria in the small intestine, and the second normal peak occurs as the lactulose enters the colon. If the baseline levels of hydrogen rise by >20 ppm after ingestion of lactulose, this can also indicate a positive test. Recently, a number of studies have demonstrated the limitations of the use of lactulose in diagnosing SIBO, mainly because of the high rate of false positives.

Hydrogen breath testing may be able to diagnose only 60% of patients with SIBO. A major problem is that there is no 'gold standard' for the diagnosis of SIBO since culture of the bacteria has its own limitations. There has been much less work undertaken on combined methane/hydrogen detection for improving SIBO diagnoses. This is most likely in part because until recently, the only methane analysis equipment was expensive and needed skilled operatives.

The relationship between methane and constipation has been demonstrated. As shown in FIG. 1: Importance of Methane in SIBO Diagnosis (Pimentel et al., 2003), higher levels of methane are indicative of SIBO that causes constipation. Other types of bacteria can produce higher levels of other gases (such as $H_2$) and cause diarrhea and related GI issues. This relationship is further described in the journal of breath research (B P J de Lacy Costello 2012).

Research has also shown a high correlation (78%) between SIBO and IBS. The SIBOTest Company also suggests that a faster manifestation of IBS symptoms after a meal (5-20 mins) indicates a SIBO-related IBS, versus patients with IBS that is unrelated to SIBO (1hr). They also suggest other indicators such as the effect of fiber, antibiotics, probiotics, and food poisoning. One group (B P J de Lacy Costell 2008) used ethanol and ammonia as target gases, possibly as a substitute for methane. This might be because methane is a relatively difficult gas to measure at low concentrations, whereas ethanol detectors are widely available, such as in breathalyzers.

SUMMARY

Accordingly, consumption of certain foods has been shown to be linked to increased gas production which is linked to a variety of illnesses including SIBO. However, the precise foods and quantities responsible for excessive gas production in each individual are burdensome to determine. For instance, in order to test for SIBO, an individual must come to a lab for a test of the gases or breathe into a bag and send it in for analysis. It is thus impractical to test the exhaled gases of the patient over many different meals and over a longer period of time.

Therefore, because intestinal gases must be tested in isolated cases, and usually after a high sugar meal, most individuals cannot determine or correlate SIBO or its symptoms to specific food items. Accordingly, it is difficult to acquire enough information on the gases produced in a particular individual to form conclusions about the food consumption patterns likely leading to excessive gas production. There is thus a need for a portable, SIBO testing device that a patient could use to frequently test their breath gas levels while simultaneously enter and store information about the time and content of meals consumed prior to testing. With this information and appropriate data analysis, the patients will then be able to discover correlations between the foods they eat and their SIBO symptoms and gas levels.

Accordingly, systems and methods have been developed for implementation of a portable SIBO testing system for convenient sampling of intestinal gases exhaled from a patient's breath. These devices may be in the form of a hand held meter that would integrate with a smartphone or other device with an application that can record data relating to food consumed by a user. Various technologies may be utilized to measure the levels of gases exhaled by a user, which may include (1) sorbent based technology and (2) membrane based technology, or other technologies.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

Figure 1:
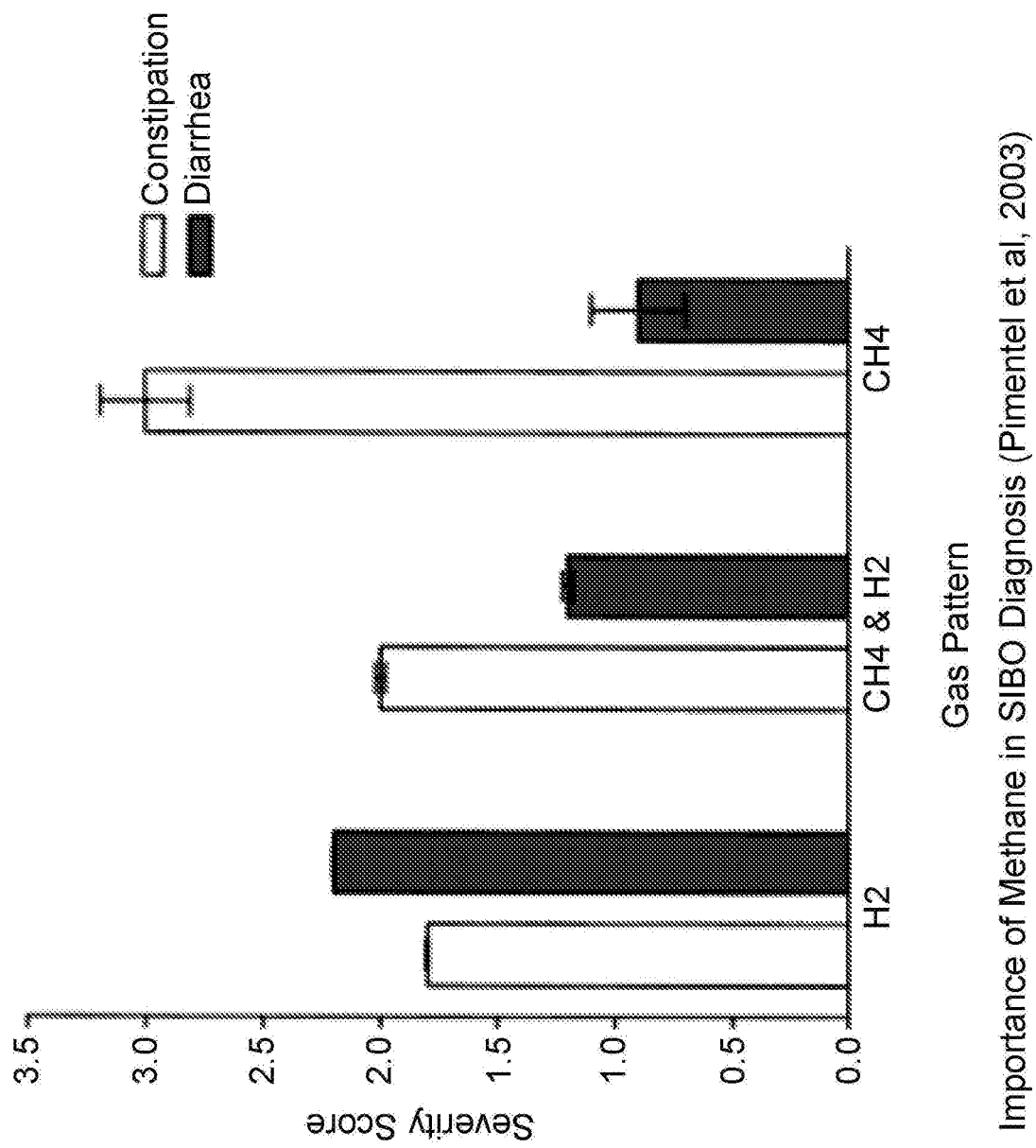
FIG. 1 depicts, in accordance with various embodiments of the present invention, a bar graph showing the importance of Methane in MO Diagnosis (prior art)

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

As described above, consumption of certain foods has been shown to be linked to increased gas production which is linked to a variety of illnesses including SIBO. However, the precise foods and quantities responsible for excessive gas production in each individual are difficult to determine. For instance, in order to test for SIBO an individual must come to a lab for a test of the gases or breathe into a bag and send it in for analysis. Therefore, it is impractical to test the exhaled gases of the patient over many different meals and over a longer period of time.

Therefore, because intestinal gases must be tested in isolated cases, and usually after a prescribed, high sugar meal, most individuals cannot determine or correlate SIBO or its symptoms to specific food items, quantities and times. Accordingly, it is difficult to acquire enough information on the gases produced in a particular individual to form conclusions about the food consumption patterns likely leading to excessive gas production. Therefore, there is a need for a portable, SIBO testing meter for home or clinical use that a patient could use to test after a variety of meals and time points, and simultaneously log information about the time and content of meals consumed prior to testing.

A device allowing for frequent use would provide users a system to frequently and consistently monitor their exhaled gas and associated bacterial levels. With this information and appropriate data analysis, the users will then be able to discover correlations between the foods they eat and their SIBO symptoms and gas levels.

Accordingly systems and methods have been developed for a gas testing device (e.g. portable SIBO testing meter) for convenient testing of intestinal gases exhaled from a patient's breath. These devices may be in the form of a hand held meter that would integrate with a smartphone or other device with an application or other software that can record data relating to food consumed by a user. Various technologies may be utilized to measure the levels of gases exhaled by a user, which may include (1) sorbent based technology and (2) membrane based technology.

Sorbents

One potential technology to measure the aforesaid gas levels includes certain sorbent technologies. In general, these are substances that absorb gases. In order to measure a gas concentration using sorbents, the sorbents can be first weighed, then exposed to the gas. After exposure, the sorbents can be weighed again to determine the increase from the added mass of the absorbed gas. Alternatively, the change in mass may be measured by other means such as luminescence, color, transparency, conductivity, or resonance.

The following formula may be utilized to determine the concentration of $H_2$ in exhaled breath gases based on weighing the sorbents:

$$\frac{V_{Lung}}{V_{per\,mol\,of\,air}} * C_{H_2} = N_{H_2}$$

$$\frac{5\,L}{24\frac{L}{mol}} * 1\,ppm = 2 \times 10^{-7}\,mol$$

$$N_{H_2} * M_{Hydrogen} = Total\,Weight_{Hydrogen\,per\,breath}$$

$$2 \times 10^{-7}\,mol * 1\frac{g}{mol} * 2 = 4 \times 10^{-7}\,g = .4\,\mu g\,(per\,breath)$$

Where;
V—Volume (litres)
C—Concentration
N—Number of mols (per breath)
M—Molecular mass of hydrogen atoms (grams)

$CO_2$ (40000 ppm), $H_2S$ (1 ppm) and methane (1 ppm) can be calculated in a similar manner and require scales sensitive to 0.6 g, 6 pg, and 3 pg respectively. Technology such as a quartz crystal microbalance may be utilized to detect weights to that level of precision.

In some embodiments, sorbent materials may require a resetting process after each use to expel all of the absorbed gases. For instance, some sorbents require a heating cycle to force the sorbent to release the stored gas, or some similar process. In other embodiments, a sorbent material may be selected which rapidly releases the absorbed gases. Accordingly, devices utilizing sorbents may include a heating element or other processing technology that would be triggered after each use to expel the gases. In other embodiments, the sorbents may be disposed of and replaced instead of being reset, but would need to be mounted to the weight measurement device.

Types of sorbents that may be utilized include immobilized amine, aminosilane, and organoclay sorbents. The amine sorbents, for example, may be regenerable. Some examples of suitable sorbents include high performance hollow microspheres, hollow fibers and supported liquid membranes. Specifically, the high performance hollow microspheres include amine microspheres. In one example, the hollow microspheres may be made of biocompatible materials for use in medical applications. The hollow microspheres have geometries that allow for detection of several gases. Further, the organoclay sorbents may be used for $CO_2$ and $H_2S$ detection. In one example, the organoclay sorbent may be an amine based sorbent. Some sorbents are designed to be regenerable such that the modified amine is regenerated in the presence of water vapor.

Examples of sorbent based technology and methods used for detecting gases are described in, for example, U.S. Pat. No. 8,500,854, issued on Aug. 6, 2013, titled Regenerable Sorbent Technique for Capturing $CO_2$ using Immobilized Amine Sorbents, and U.S. Pat. No. 7,288,126, issued on Oct. 30, 2007, titled High Capacity Immobilized Amine Sorbents, both of which are incorporated by reference herein in their entirety. Sorbent based technology is advantageous because of its small size and could therefore be integrated into a portable SIBO meter.

Membranes

In some embodiments, membrane based technology may be utilized to determine the concentrations of breath gases. For instance, membranes could first be utilized to selectively filter gases of interest. Then, another sensor technology may determine the concentration of the isolated gas that has permeated through the other side of the membrane. For example, pressure sensors (to detect partial pressure changes), gas chromatography, or a simple counter could be utilized. In some embodiments, the combination of membranes with other sensor technologies may enhance the selectivity of the device.

Some examples of membranes to be incorporated into the devices and methods disclosed herein include flat sheet membranes, hollow microspheres and mixed matrix membranes. Mixed matrix membranes, in particular, may be advantageous as they have different levels of bulk and surface porosity as well as customizable inner and outer diameter dimensions. The geometries of the membranes allow for maximum detection of several gases. Specifically, mixed matrix membranes with metal organic frameworks may be used for detection of $CO_2$ and $CH_4$. Membrane based technology is advantageous because of its small size and could therefore be integrated into a portable SIBO meter. For instance the size and flexibility of membranes allow them to be integrated in smaller channels of a SIBO meter, and therefore they are particularly advantageous to this technology.

Breath Intake Device

In some embodiments, the SIBO meter may include a breath intake device for measuring the flow and directing the gases to the components that measure the levels of gases. In one example, a detector may include sorbents and/or membranes connected to an electrode. In some embodiments, these may include a tube or other structure. In another example, the device may include a quartz microbalance. In another example, the gas volume may be measured via a colorimetric assay and/or by tin oxide. In another example, the device may contain individual cartridges in order to detect specific gases. For example, the device may contain individual cartridges for $CO_2$, $CH_4$, and/or $H_2S$ respectively. The cartridges may be disposable such that the device may last for multiple uses (e.g., 300 readings) and or a predetermined amount of time (e.g., 1-2 years). In another example, each disposable cartridge may last for a number of uses (e.g., 10-50 readings) and/or a predetermined amount of time (e.g., 1-3 months).

In some embodiments, devices and methods disclosed herein may include a flow control and moisture control module, to prevent moisture and variations in the flow and partial pressures of gases from skewing the results. Additionally, the device may include a backflow prevention mechanism so that exhaled air is does not escape and remains isolated for testing. Moisture control may be included before or after the flow regulator to adjust the air humidity to a consistent level or to remove all moisture if sensor cross-sensitivities exist, or to prevent general moisture contamination.

The carbon dioxide sensor, which may work in conjunction with the flow sensor, is then exposed to the air to quantify the lung air volume that is passed through the device (with exhaled air nominally at 4% $CO_2$ and not largely influenced by SIBO levels.

Portable Hydrogen Device

In some embodiments, a small, portable device is disclosed. In some embodiments, the portable device may utilize an electrochemical sensor to measure $H_2$ and may also have a method of normalization such as $CO_2$ detection. In some embodiments, the device may communicate and send data to a smartphone via Bluetooth, USB, cellular, or other connection transmit its data for processing and display. In some embodiments, the device can also be built as an iPhone attachment, physically attaching to the device.

Colorimetric Sensor Device

In some embodiments a colorimeter sensor device may be utilized for detecting the gas concentrations. For instance, colorimetric strips (e.g., a separate strip each for each of $CO_2$, $H_2$ and $H_2S$) that change color in coming into contact with gases of interest may be implemented to determine the relevant gas concentrations. In some embodiments, the test strips will change color in proportion to the concentration of given gases, or will cause a certain portion or distance of the test strip to change color.

This distance, along with the intensity of color change may then be detected by a photo detector and quantified. The advantages of this embodiment are speed, continued accuracy over time, low cost of device, lack of requirement for calibration, and simplicity. The benefits of this configuration are the lack of requirement to heat up, pump air, or run any sort of cleaning procedure, and the battery life would be excellent. It would also be resistant to shock and abuse. The consistent accuracy and reliability means this embodiment could be approved for clinical use, should that be an advantageous business decision.

The device may also incorporate a photo-detector system to determine the distance and density of the color change, though this practice is well established and generally of an acceptable accuracy. An alternative to this is to have the user read this value, offering an electronics free option. Electronic free volume measurement devices are also available on the market.

Portable Clinical Device

In some embodiments, a clinical grade, handheld analysis device may be utilized that can detect $CO_2$, $H_2$, and $H_2S$ using durable and reusable sensors. In some embodiments, it may operate from a rechargeable battery. In some embodiments, $CO_2$ could be detected using an NDIR cell, and $H_2S$ could be detected with a fuel cell sensor. $H_2$, as in some embodiments, can be detected with an Alphasense electrochemical cell or equivalent.

In some embodiments, it can connect to a smartphone app via Bluetooth to upload data. That data would be processed both on the smartphone and by cloud servers that also have the ability to share results with healthcare providers. The device would also accept user inputs such as time stamped activities and clinically relevant symptoms.

Full Clinical Device

In some embodiments, disclosed is a clinical medical device capable of detecting $CO_2$, $H_2$, $CH_4$, and $H_2S$ with a high degree of accuracy. It would use a Gas Chromatograph, Ion Mobility Spectrometer, TDLS, or a Flame Ionization Detector, or a combination of these technologies with the smaller sensors from the portable devices. As with the other devices, readings would be available very shortly after a sample passed through the detector. Some of these comprehensive sensor technologies might be expensive and would be more amenable to being a centralized tool to which samples are sent.

For this embodiment, the patient may blow into a breath collector, or as an alternate embodiment, the clinician could attach a bag to the connector that the patient has filled previously by blowing into the bag. After analysis, the data would be printed off or sent to a PC, and the clinician may be required to run a purging gas (e.g. for re-calibration and/or clearing of the breath gases) through the device (such as inert nitrogen, or another gas with a precise $H_2S$, $H_2$, $CO_2$ and $CH_4$ concentration).

Computer Application

The devices disclosed herein may interface with various computing devices that are configured with instructions to allow entry and storage of data relating to consumption of food. An essential tool for both the home and clinical devices will be the associated software applications in the form of a smartphone app or other software program. The device will either connect to the smartphone via Bluetooth or hardwire, allowing data transfer. The application will connect to the internet to perform some combination of updates, cloud data storage, or information processing. A clinical version might be setup with a dedicated tablet, hardwired to the device, to display and process results.

For the home use device, the software may be implemented to help the patient make their own choices and conclusions from the data regarding how their diet affects their SIBO readings and how they should change their diet. It is also important to match activities (such as eating) with measurements in a way the patient can understand. These requirements are not a significant technical risk. Many devices with this embodiment are being engineered today, and many engineers are capable of such projects.

Methods for Acquiring Data from a Patient

Various protocols may be utilized to determine when a patient is to test their gases, and what symptom and meal information a patient enters after testing. For instance, in some embodiments, the patient may only use the device when the feel the symptoms of SIBO. In those embodiments, the user interface of the application may ask the patient which of the predefined categories of symptoms the user is experience, for instance: bloating, constipation, diarrhea, etc.

Then, the application may request what type of food the patient ingested within the past 12 hours, 6 hours, 4 hours, 20 minutes or other relevant time frame in terms of SIBO gas production. In some embodiments, the system will have certain predefined categories of food and amounts. For instance, the program may have sugar based, fat based, or protein based food categories. In other embodiments, the program may have an index of food categories that are linked in a database to certain nutritional values or ingredients relevant to SIBO. For instance, the types of sugars in each food may be indicated, including glucose, sucrose, lactose, etc.

The system may also require and save the data in a memory, which may be shared with a server or may be saved locally. In some embodiments, the application will ask a user for information, including sex, height, weight, age, and SIBO related characteristics. This information may be utilized in the cloud to correlate similar patients' ingestion and related gases. Additionally, specific patients may create specific combinations or types of gases or have certain profiles of bacteria.

In some embodiments, the patient may undergo a lactulose or glucose breath test in order to test the gases produced in response to certain substances. The caregiver may also instruct the patient to fast for one hour, two hours or other specified time to determine a methane concentration in the breath of the patient.

Analysis of Data for SIBO and Other Correlations

In some embodiments, once the data is acquired, it may be logged for analysis by the patient. In other embodiments, the processor or associated control systems may analyze the data. For instance, the device may look in patterns of correlating symptoms to certain foods, times and/or exhaled gases. For instance, in some embodiments, the system may correlate a particular gas level (e.g. crosses a threshold level known to be abnormal or has a characteristic double spike instead of single) with eating a certain amount of a certain type of sugar within a specific amount of time. In some embodiments, machine learning algorithms may be utilized to match the types of conditions optimal for SIBO for a given patient.

In other embodiments, the correlation may be more straightforward, and correlate the frequency of SIBO symptoms with eating a certain type of foods within a predefined time window. In other embodiments, the system may correlate or determine, for instance, the average $H_2$, $H_2S$, or $CH_4$ levels or peak of the levels within a certain time windows after eating certain foods. The system could then determine whether certain classes of foods (e.g., foods containing sucrose) result in a spike of a certain gas or combination of gases above a pre-defined threshold. In other embodiments, the system could output a graph of the average and standard deviation of gas levels after eating certain types or classes of foods.

In some embodiments, the system may correlate a level of hydrogen change over time or after undergoing a lactulose or glucose regimen. Additionally, a system as disclosed herein may additional test both the hydrogen and methane before and after ingestion of sugar and lactulose to detect the change in concentration of the cases. The system could then process the data to determine a methane calibrated hydrogen change. The system could then calibrate the change in hydrogen to the current methane production for the patient to determine a more accurate indication of whether a patient has SIBO.

In some embodiments, the system may output data in the form of a chart to allow a user an easy and convenient method for analyzing the gas levels and associated foods. In some embodiments, the foods could be ranked in terms of the amount of increased gas production they result in.

Accordingly, consumption of certain foods has been shown to be linked to increased gas production which is linked to a variety of illnesses including SIBO. However, the precise foods and quantities responsible for excessive gas production in each individual are difficult to determine. For instance, in order to test for SIBO an individual must come to a lab for a test of the gases or breathe into a bag and send it in for analysis. Therefore, it is impractical to test the exhaled gases of the patient over many different meals and over a longer period of time.

EXAMPLES

Following are examples of various devices that may be utilized according to the present disclosure. These examples are not intended to be limiting, and only provide examples of various features and methods that may be employed for efficiently testing breath gases in a patient.

Figure 1A:
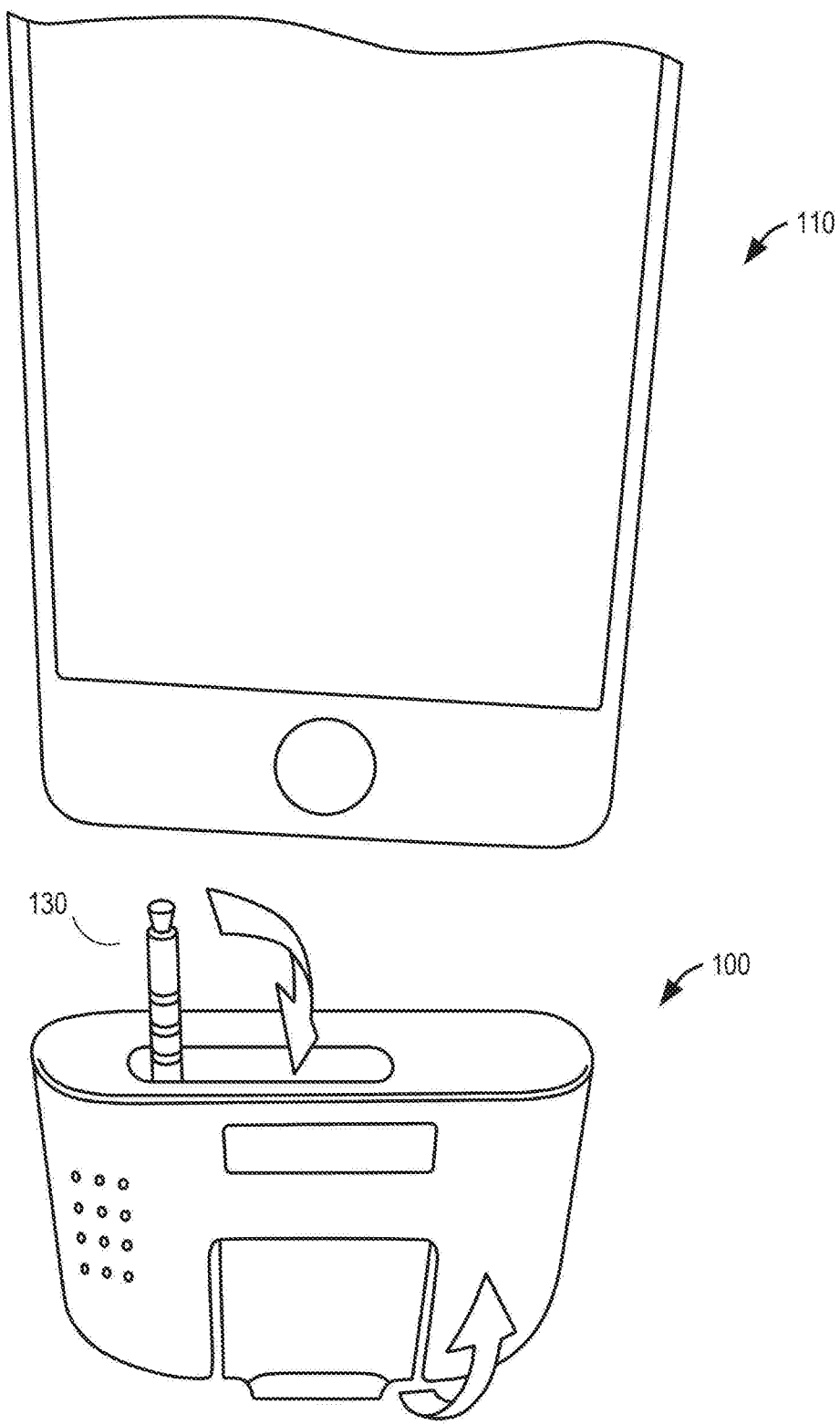
FIG. 1A depicts, in accordance with various embodiments of the present invention, a perspective view of a gas detection device that interfaces with a mobile device.
Figure 1B:
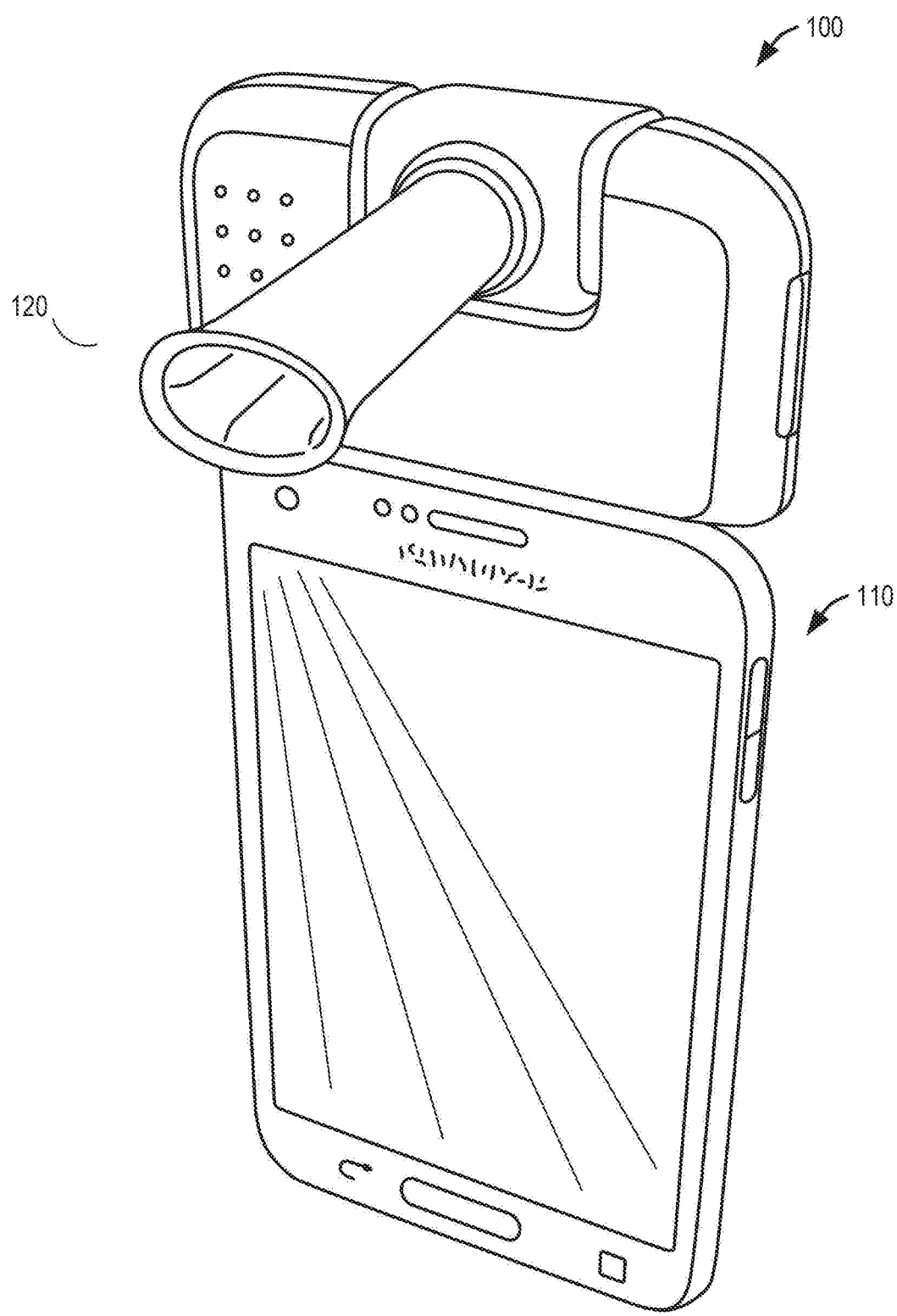
FIG. 1B depicts, in accordance with various embodiments of the present invention, a perspective view of a gas detection device that interfaces with a mobile device.

FIGS. 1A-1B illustrate an example of an embodiment of a gas detection device 100 that may be attached to a mobile device 110. The device includes a mobile interface 130, which may be any standard mobile connection for the iPhone, blackberry, other mobile phone, including standard jack (as illustrated). In some embodiments, the connection will be a Bluetooth, Wi-Fi or other wireless connection.

The device also includes a retractable mouthpiece 120 pictured in FIG. 1B. In some embodiments, the connection to the mouthpiece 120 will allow the mouthpiece 120 to be removed, and the connection to be rotated into place inside the gas detection device 100. In some embodiments, the mouthpiece 120 can be stored separately or replaced. This will allow the mouthpiece to remain sanitary, and easily connected for each breath test.

Figure 2:
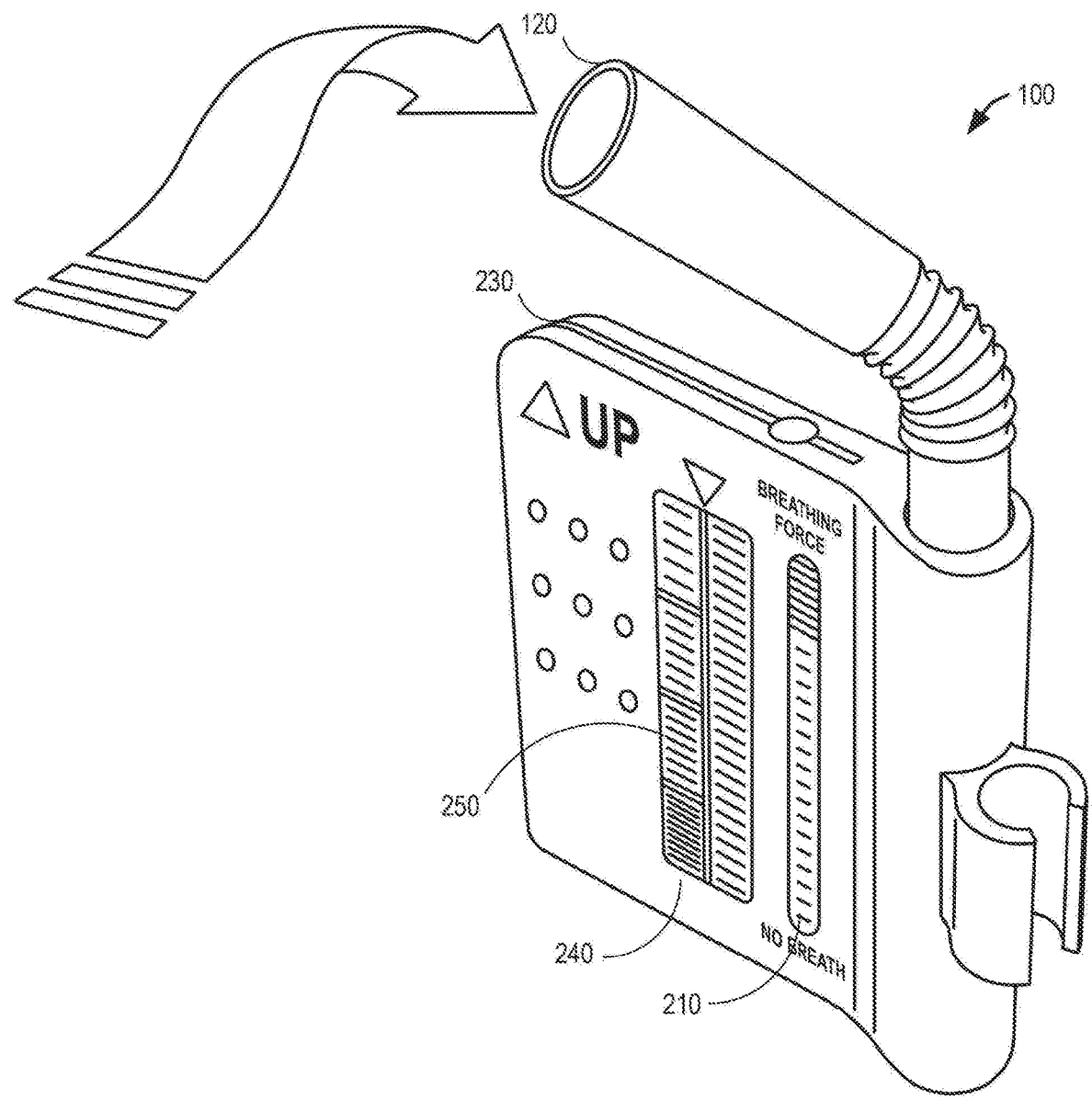
FIG. 2 depicts, in accordance with various embodiments of the present invention, a perspective view of a gas detection device.

FIG. 2 illustrates an embodiment of a gas detection device 100 that includes a mouthpiece 120 and a flow meter 210. In some embodiments, the gas detection device will utilize test strips 220 with colorimetric based gas sensing technology. In some embodiments, the test strips 250 will be inserted into an opening or slot 230 of the gas detection device 100. The device may include a display or indicator 240 indicating gas levels. In some embodiments, the test strips 220 may be visible behind a glass or plastic, transparent window that is the display 240.

When a patient breathes into the mouthpiece 120 the flow meter will provide feedback to the patient regarding the proper strength of breath. Then the test strips may change color based on the amount of gases contained in the patient's breath. Accordingly, an optical reader may translate the color change into gas concentrations or the patient may get a qualitative or quantitative assessment by visually inspecting the color change. In some embodiments, the test strips provide a threshold indication of whether the patient has gases that are indicative of SIBO or another condition (e.g., more of a binary or rudimentary measure). In other embodiments, precise gas levels will be calculated and stored.

Figure 3A:
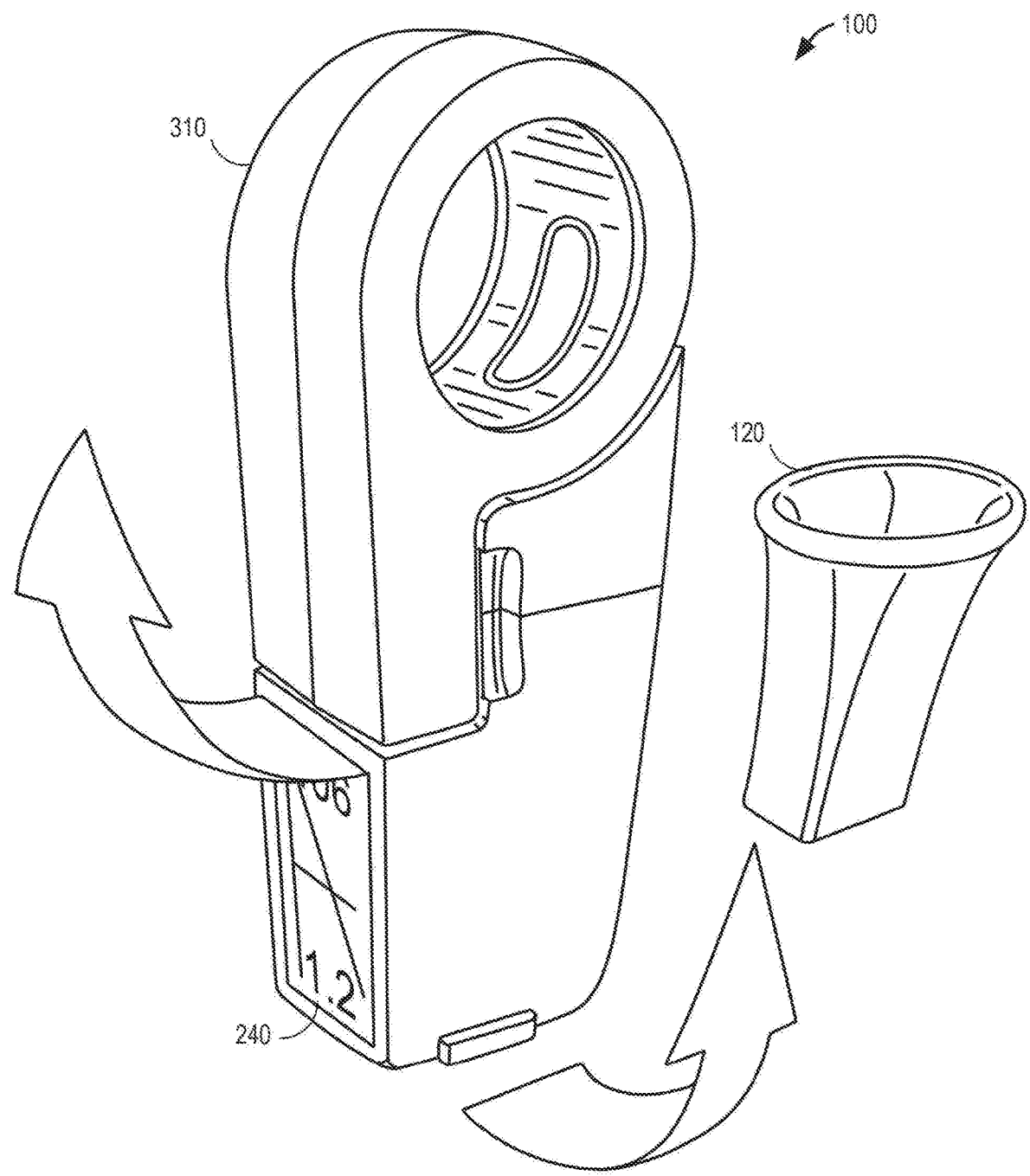
FIG. 3A depicts, in accordance with various embodiments of the present invention, a perspective view of a gas detection device.
Figure 3B:
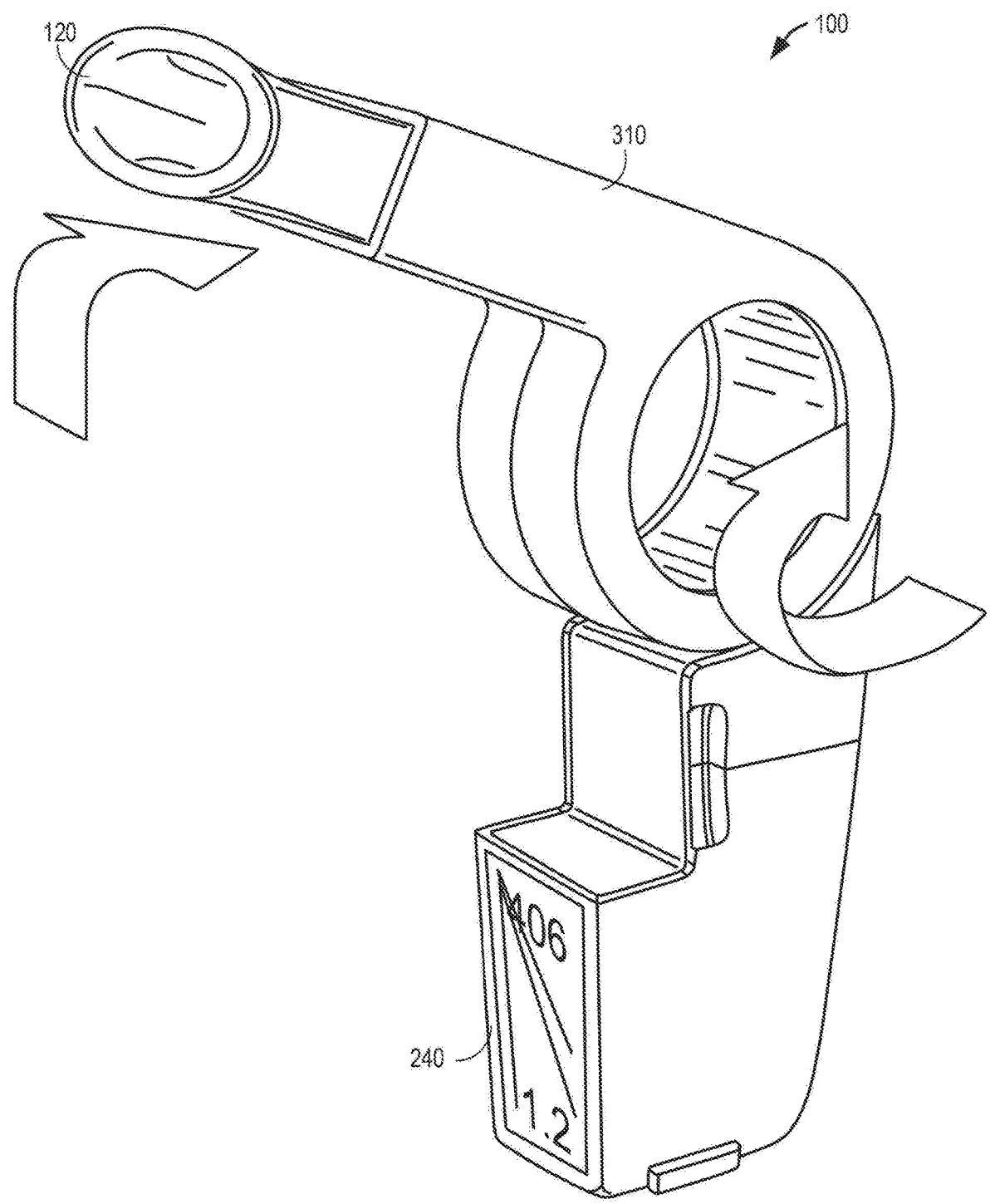
FIG. 3B depicts, in accordance with various embodiments of the present invention, a perspective view of a gas detection device.

FIGS. 3A-3B illustrate embodiments of a gas testing device 100 that include a rotatable breath collector 310 for directing the exhaled breath gases to the testing chambers and a mouthpiece 120. This embodiment includes a display 240 for displaying the results of the testing. FIG. 3B illustrates the breath collector 310 rotated out into a position in which the patient may breath into the mouthpiece 120 and breath collector 310 can then collect the breath gas. As illustrated, after rotating out the breath collector 310, the mouthpiece 120 may be attached. This rotation allows the passageways of the breath collector 310 to remain protected an inaccessible while not in use, and allows the device to remain compact.

Figure 4:
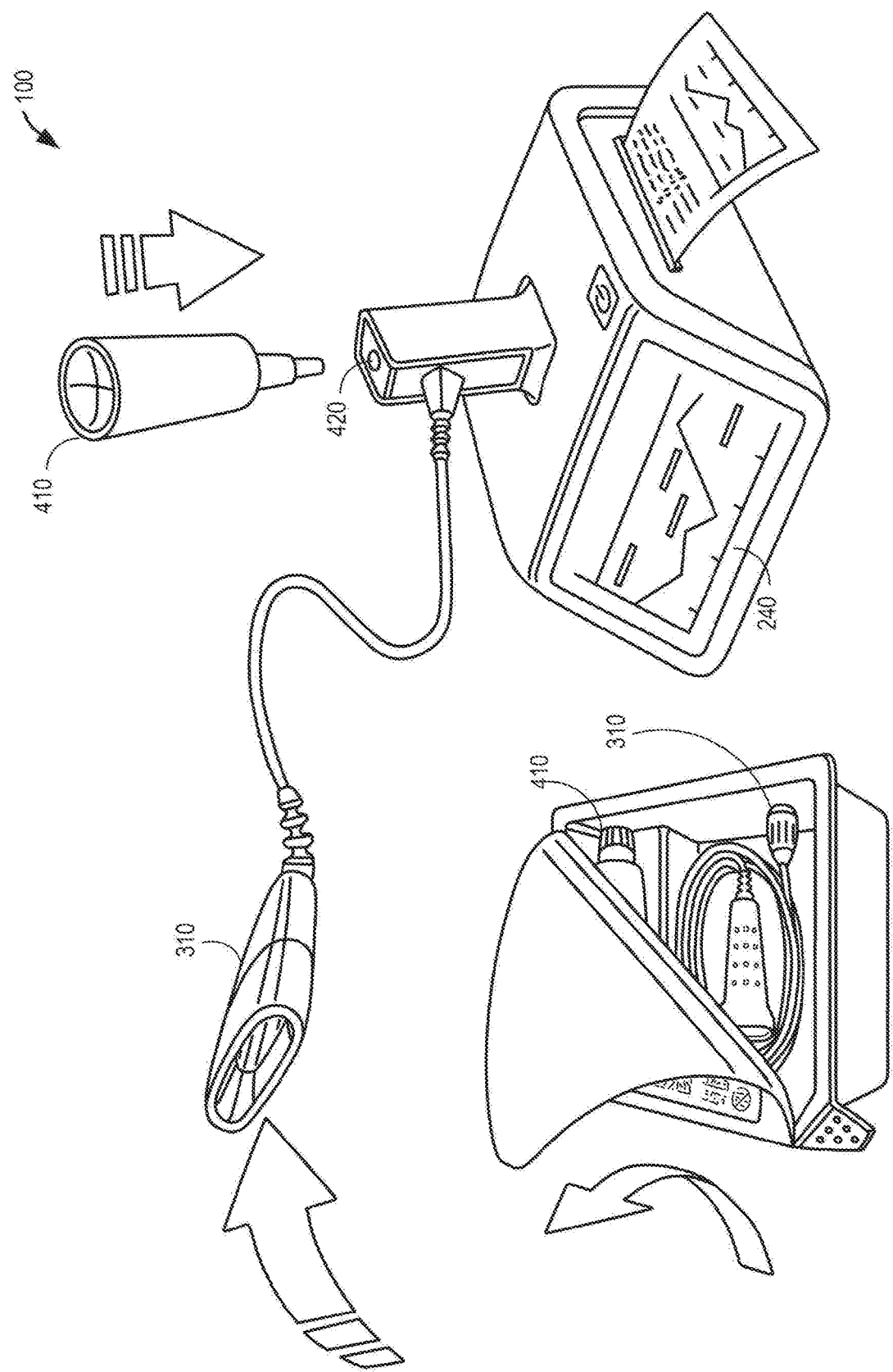
FIG. 4 depicts, in accordance with various embodiments of the present invention, a perspective view of a gas detection device and associated breath tube kit.

FIG. 4 illustrates an embodiment of a clinical gas testing device 100 that includes a breath collector 310, and a display 240. In some embodiments, the clinical gas testing device 100 may include a larger testing chamber and employ more precise and accurate sensing technology. In some embodiments, the clinical gas testing device 100 may include a purge canister 410 for purging the testing chamber of breath gases from a patient. This will allow the chamber to be recalibrated from a baseline gas level after each use. In some embodiments, the canister 410 and breath collector 310 will be disposable pieces, separately packaged for each use as illustrated in FIG. 4.

Figure 5:
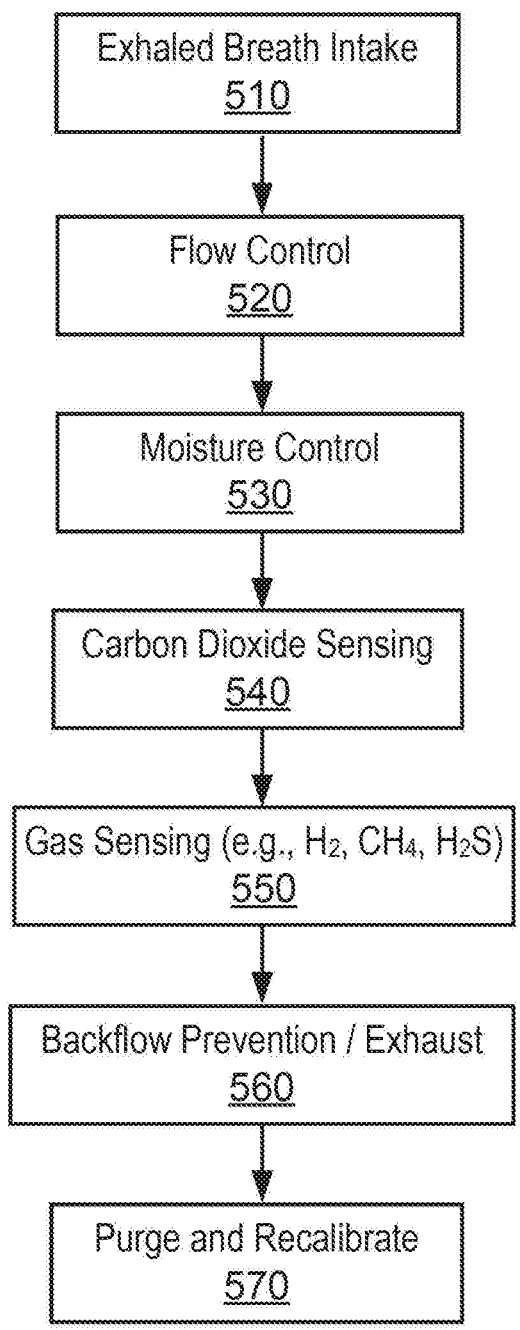
FIG. 5 depicts, in accordance with various embodiments of the present invention, a flow chart depicting a method of testing breath gases.

FIG. 5 illustrates an embodiment of a method of testing the breath gases of a patient utilizing various gas detection devices 100 as disclosed herein. For instance, first the exhaled breath is collected 510 and directed to a testing chamber. In some embodiments, a flow meter may control the flow rate of the exhaled breath being routed through the testing chamber 520. This may allow the partial pressure of relevant gases to be held constant, or to otherwise increase the accuracy of the results. After, the moisture may also be controlled 530, to avoid inaccurate sensor readings that may be caused for a variety of reasons based on the gas detection technology.

Afterward, some embodiments will include a carbon dioxide sensor 540 to use as a proxy for the amount of breath exhaled, and to correlate the levels of breath gases to the amount of $CO_2$. In some embodiments, the amount of $CO_2$ or concentration of the gas can be correlated to determine how long the air has been held in the lungs. The levels of relevant gases detected thereafter can be adjusted accordingly to the appropriate ratios.

After carbon dioxide is tested (or simultaneously or beforehand) the levels of other gases may be sensed 550 that have clinical relevancy. For example, the system may then test $H_2$, $CH_4$, and/or $H_2S$. Additionally, backflow may be prevented 560 to prevent the concentration from changing once testing has initiated in any such device. Finally, after testing, the breath gases may be purged and the device recalibrated 570. In some embodiments, the recalibration will be performed by purging the device with a canister of a gas(es) at a known concentration(s) and/or known flow rate(s). In other embodiments, a fan and door may open to allow ambient air to enter the device.

Example—Methane and Hydrogen Interaction

The lactulose breath test is increasingly being used to diagnose small intestinal bacterial overgrowth (SIBO). In the last decade, data have accumulated about the importance of methane in breath testing especially in the context of constipation. During the production of methane, methanogenic archaea in the gut utilize 4 hydrogen ($H_2$) gas molecules to produce a single methane ($CH_4$). Based on this stoichiometry, the level of hydrogen on breath testing (and thus the interpretation of the breath test) could be affected when detectable methane (and hence methanogens) are present. The inventors performed a study of a large scale breath test database to determine the effect of methane on the interpretation of hydrogen results.

Consecutive patients presenting to a tertiary care medical center between Nov. 2005 and Oct. 2013 for lactulose breath testing were eligible for review. For the breath test, subjects presented after a 12 hour fast. After a baseline breath sample, 10 g of lactulose was administered followed by subsequent breath samples every 15 minutes for a minimum of 90 minutes. Breath samples were then analyzed on a Quintron SC or Breathtracker™ gas chromatograph (Quintron Instrument Co., Milwaukee, Wis.) to measure hydrogen and methane after correction for $CO_2$. Breath methane was defined as ≥3 ppm any time during test. The remaining subjects were deemed non-methane subjects. Subjects were excluded if they were non-gas producers (neither hydrogen nor methane ≥3 ppm at any time during test). Interactions between hydrogen and methane were examined by comparing methane and non-methane breath tests.

Figure 6:
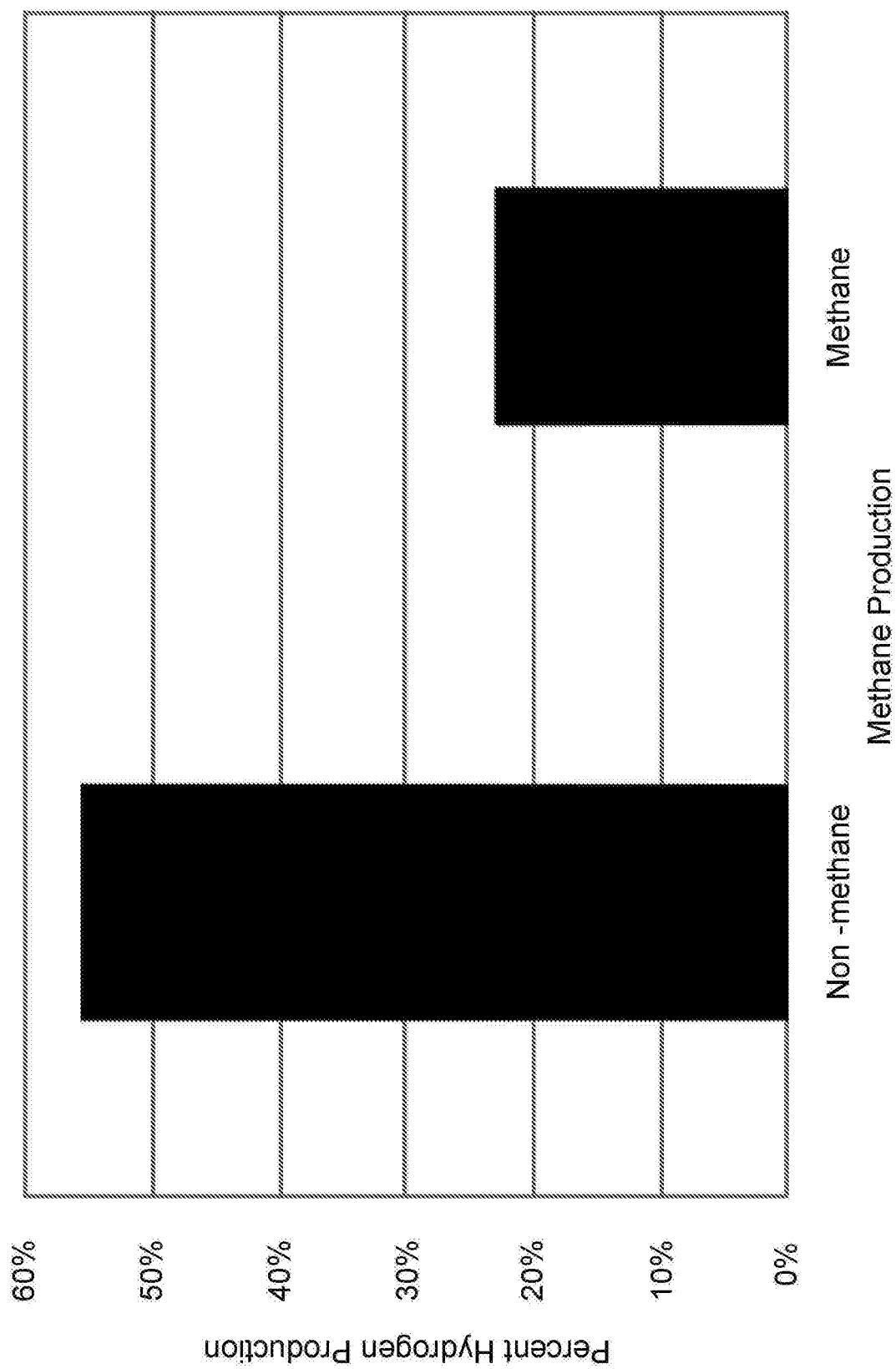
FIG. 6 depicts, in accordance with various embodiments of the present invention, a bar graph showing percent hydrogen production for methane and non-methane producers.

A total of 14,847 breath tests were conducted during this time of which 804 (5.4%) were non-methane, non-hydrogen producers. Of the remaining 14,043 tests (71% female, mean age=47.4±18.3 yrs), 2412 (17.2%) were positive for methane. Irrespective of whether 60 or 90 minutes was used to interpret $H_2$ changes consistent with SIBO, breath tests with methane had a significantly lower breath $H_2$ (see Table 1 and FIG. 6). Examining the change in hydrogen production from baseline, for 60 or 90 minute breath testing interpretation, breath tests with methane also had a reduced rise in hydrogen (Table 1 and FIG. 6 from baseline compared to non-methane breath tests. Furthermore, there were significantly fewer breath tests meeting ≥20 ppm rise of $H_2$ to be considered SIBO in methane producers (23.1%) compared to non-methane subjects (55.7%) (OR=0.20, 95% CI=0.18-0.22) (FIG. 6).

TABLE 1

|  |  | Non-methane | Methane | P-value |
|---|---|---|---|---|
| 90 minute breath test (ppm) | AUC of $H_2$ | 85.5 ± 0.6 | 53.7 ± 1.4 | <0.0001 |
|  | Change in $H_2$ | 25.3 ± 0.2 | 10.7 ± 0.4 | <0.0001 |
| 60 minute breath test (ppm) | AUC of $H_2$ | 36.4 ± 0.3 | 28.1 ± 0.8 | <0.0001 |
|  | Change in $H_2$ | 9.6 ± 0.1 | 4.8 ± 0.2 | <0.0001 |

Based on the results, the presence of methane is associated with a significant reduction in hydrogen levels, and dramatically alters the interpretation of hydrogen in breath testing for identification of bacterial overgrowth. Based on these findings, it is imperative to report methane production in clinical reporting and research studies.

Fasting Breath Test for Methane

Excessive methane production can be associated with constipation and bloating. Eradication of methanogen bacteria and decreasing methane production have been shown to improve such symptoms. In a recent consensus meeting at Digestive Disease week 2015, a methane level of >10 part per million (ppm) during a standard 2 hour breath testing was considered the cut off for excessive methane production. Unlike hydrogen gas, patients with excessive methane continue to excrete high levels of methane in the fasting state. Hence, the accuracy of a single fasting measurement of methane was compared to lactulose breath testing as gold standard. METHODS: A database of 14847 consecutive lactulose breath tests (71% females) from Nov. 2005 to Oct. 2013 was developed at a tertiary center. A deterministic record linkage was performed to exclude repeated studies of 12183 subjects. In all subjects, after 12 hours of fasting, exhaled methane, hydrogen and carbon dioxide were measured. Patients received lactulose (10 g) and measurements were repeated every 15 minutes for at least 2 hours. A patient was classified as excessive methane producer if at any point of the study a methane level of ≥10 ppm was detected (gold standard). Test characteristics of various fasting methane levels were compared to gold standard. A sensitivity of ≥95% and a specificity of >98% was chosen as a priori for test performance. Fisher exact test was used for comparisons. RESULTS: Of 12183 subjects, 1891 (15.5%) were excessive methane producers (68.5% female; mean age 51.9±17.7; age range 3-97 years). Accuracy of various fasting methane levels to identify these patients are shown in Table 1. Although, all single fasting methane measurements performed well, a cut-off of ≥5 ppm was chosen with sensitivity, specificity, positive predictive value and negative predictive value (NPV) of 96.1%, 99.7%, 98.5% and 99.3%, respectively. (Table 2 & 3) Performance of the test was not statistically confounded by age or gender. (Table 4)

In the largest database of lactulose breath tests analyzed to date, a single fasting measurement of exhaled methane is highly sensitive and specific to identify excessive methane producers as compared to full lactulose breath testing. This approach can significantly decrease the cost, shorten the study time and omit the bothersome symptoms associated with lactulose intake. Age and gender do not affect the accuracy of fasting methane levels.

TABLE 2

Test characteristics of various single fasting methane levels as compared to the gold standard test.

| Fasting methane level (ppm) | Sensitivity (95% CI) | Specificity (95% CI) | PPV (95% CI) | NPV (95% CI) | +LR | −LR |
|---|---|---|---|---|---|---|
| ≥10 | 86.4 (84.8-87.9) | 100* | 100 (99.8-100) | 97.6 (97.3-97.8) | Not applicable* | 0.14 |
| ≥9 | 88.8 (87.3-90.2) | 100 (99.9-100) | 99.9 (99.6-100) | 98 (97.7-98.2) | 4569 | 0.11 |
| ≥8 | 90.7 (89.3-92) | 99.9 (99.9-100) | 99.7 (99.2-99.9) | 98.3 (98.1-98.6) | 1557 | 0.09 |
| ≥7 | 93 (91.8-94.1) | 99.9 (99.8-99.9) | 99.3 (98.7-99.6) | 98.7 (98.5-98.9) | 736 | 0.07 |
| ≥6 | 94.6 (93.4-95.5) | 99.7 (99.6-99.8) | 99.1 (98.5-99.5) | 99 (98.8-99.2) | 572 | 0.05 |
| ≥5 | 96.1 (95.1-96.9) | 99.7 (99.6-99.8) | 98.5 (97.8-99.0) | 99.3 (99.1-99.4) | 353 | 0.04 |
| ≥4 | 97.3 (96.4-97.9) | 99.6 (99.4-99.7) | 97.7 (96.9-98.3) | 99.5 (99.3-99.6) | 227 | 0.03 |
| ≥3 | 98.8 (98.2-99.3) | 99.3 (99.1-99.4) | 96 (95.1-96.9) | 99.8 (99.7-99.9) | 132 | 0.01 |

*Single methane level equal or greater than 10 ppm fulfills the gold standard test for methane positivity.
CI: Confidence interval;
NPV: Negative predictive value;
PPV: Positive predictive value.

TABLE 3

2 × 2 contingency table for fasting methane level ≥5 ppm as compared with gold standard test

|  | Gold Standard (Full breath test) | |
|---|---|---|
|  | Methane producer | Non-Methane producer |
| Fasting methane ≥5 ppm | 1817 | 28 |
| Fasting methane <5 ppm | 74 | 10264 |
|  | 1891 | 10338 |

TABLE 4

Robust performance of fasting methane level ≥5 ppm based on gender and age with overlapping confidence intervals.

|  | Sensitivity (95% CI) | Specificity (95% CI) |
|---|---|---|
| Females (n = 8647) | 95.8 (94.6-96.9) | 99.8 (99.6-99.9) |
| Males (n = 3536) | 96.6 (94.9-97.9) | 99.7 (99.4-99.8) |
| Age <18 (n = 543) | 90.7 (77.9-97.4) | 99.8 (98.9-100) |
| Age 18-65 (n = 8778) | 96.2 (95-97.2) | 99.7 (99.6-99.8) |
| Age ≥65 (n = 2682) | 96.2 (94.3-97.6) | 99.7 (99.4-99.9) |

Example—Methane Production and Age

There is mounting clinical evidence that excessive methane production can be associated with constipation and bloating. Eradication of methanogens and decreasing methane production have been shown to improve such symptoms. In human study, methanogenic colonization of the intestinal tract increases throughout childhood but reaches a peak in adolescence. However, large-scale studies are lacking to explore the demographic determinants of methane production.

A database consisting of 14,847 consecutive lactulose breath tests, performed between Nov. 2005 and Oct. 2013 in a single institution was developed. Using date of birth, medical record number, first and last name; a deterministic record linkage was performed to exclude repeated studies. Hence, a total of 12,183 breath tests were classified into six categories: 1-Normal: Methane levels <3 parts per million (ppm) and hydrogen levels <20 ppm within the first 90 minutes. 2-Positive hydrogen: Methane levels <3 ppm and hydrogen levels ≥20 ppm within 90 minutes. 3-Positive methane: Methane levels ≥3 ppm and hydrogen <20 ppm. 4-Hydrogen and methane positive: Methane levels ≥3 ppm and hydrogen levels >20 ppm within 90 minutes. 5-Flatliners: Methane<3 ppm and hydrogen≤3 ppm with variation ≤1 ppm within 120 minutes. 6-Equivocal: Hydrogen levels above 20 ppm at baseline prior to ingestion of lactulose and methane <3 ppm.

Figure 7:
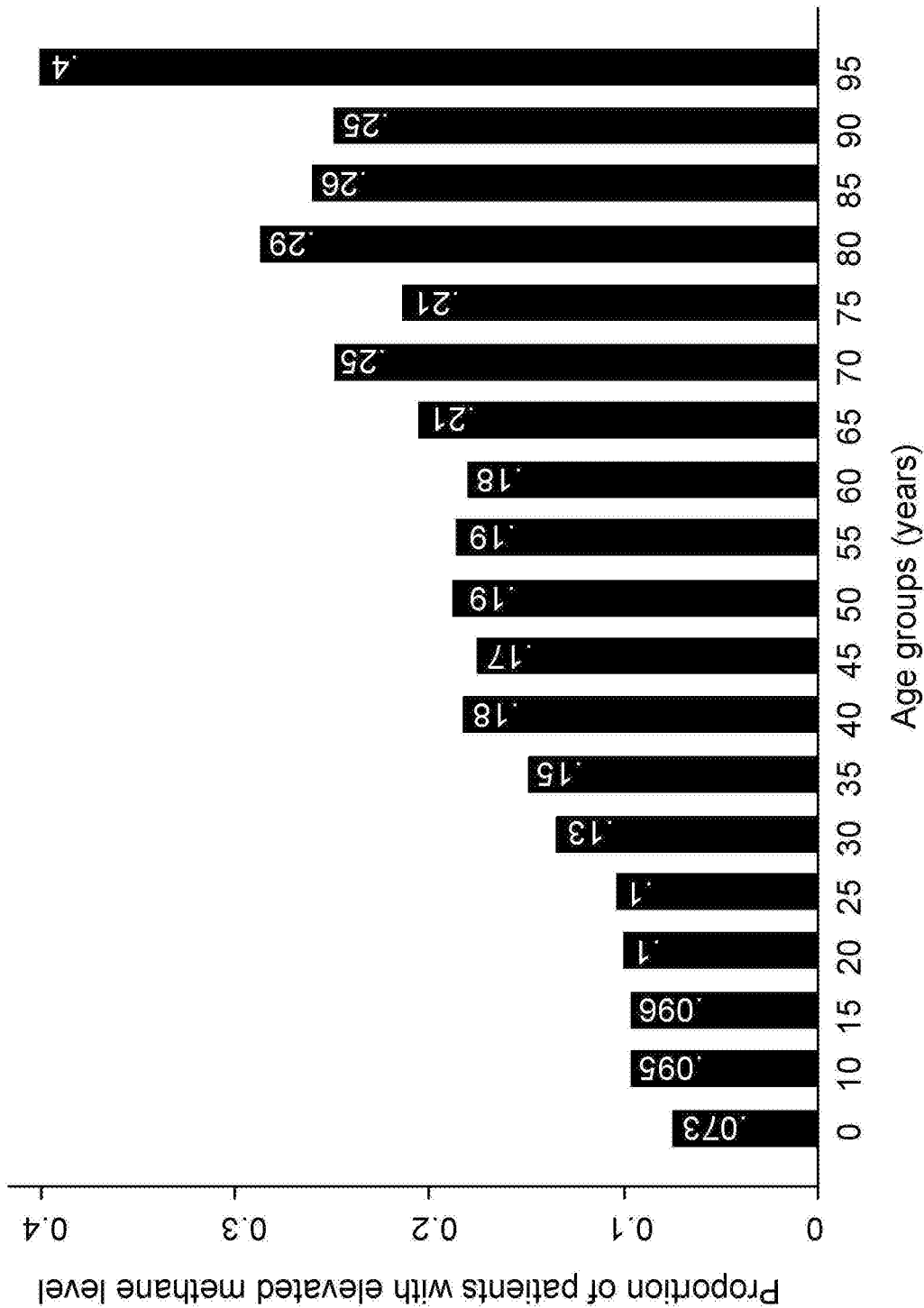
FIG. 7 depicts, in accordance with various embodiments of the present invention, a bar graph showing population of patients with elevated methane levels by age.

Of the 14.847 breath test subjects, most were females (71%). Average age at the time of breath test was 46.9±18.3 years (range 2-101). The proportions of each category of breath test result are represented in Table 1. Male subjects were significantly more likely to produce excessive amounts of methane (18.21% vs. 16.07%, $p<0.01$); however, no other significant differences existed between the two genders. Regardless of gender and hydrogen production, those producing abnormally high amounts of methane were significantly older than non-methane gas producers with a mean age of 52.3 years and an age difference of 5.8 years ($p<0.01$). The equivocal group was the youngest group with a mean age of 34.8 years ($p<0.01$). The prevalence of methane production appeared to increase with age, as shown in FIG. 7.

In the largest database of lactulose breath tests analyzed to date, the prevalence of methane gas on breath test increases by more than five-fold with age, with the oldest age group having the highest prevalence of methane producers. This finding may explain why age is a known risk factor for constipation. Finally, with a difference of approximately 2%, males were slightly but significantly more likely than females to be methane producers, the clinical significance of which has yet to be determined.

TABLE 5

Proportion of breath test categories

|  | Mean age ± SD | Female | Male | p-value | Overall |
|---|---|---|---|---|---|
| Normal Breath Test | 46.82 ± 18.37 | 31.10% | 30.51% | 0.261 | 30.90% |
| Positive $H_2$ | 45.45 ± 18.15 | 48.77% | 47.85% | 0.312 | 48.50% |
| Positive $CH_4$ | 52.33 ± 17.55 | 12.22% | 13.83% | 0.016* | 12.69% |
| Positive $H_2$ and $CH_4$ | 49.95 ± 18.46 | 3.85% | 4.38% | 0.174 | 4.01% |
| Flatliner | 47.64 ± 17.43 | 3.46% | 2.91% | 0.126 | 3.30% |
| Equivocal | 34.84 ± 16.63 | 0.60% | 0.51% | 0.541 | 0.57% |

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSIONS

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A method of determining a likelihood of the presence of small intestine bacterial overgrowth (SIBO) in patients based on an increase in hydrogen levels, the method comprising:
   receiving a first batch of breath exhaled by a patient at a first time before ingestion of a substance in a breath collector;
   routing the batch of breath through a testing chamber comprising a hydrogen and a methane sensor at a controlled flow rate;
   determining a first hydrogen gas concentration using the hydrogen sensor and a first methane gas concentration using the methane sensor in the first batch of breath exhaled by the patient;
   receiving a second batch of breath exhaled by the patient at a second time after ingestion of a substance in the breath collector;
   routing the second batch of breath through the testing chamber comprising the hydrogen and the methane sensor at the controlled flow rate;
   determining a second hydrogen gas concentration using the hydrogen sensor and a second methane gas concentration using the methane sensor in the second batch of breath exhaled by the patient;
   comparing the first and second concentrations of hydrogen gas to determine a change in hydrogen gas concentration after ingesting the substance;
   determining a methane calibrated change in hydrogen gas concentrations based on at least one of the first and second methane concentrations;
   determining whether the methane calibrated change in hydrogen gas concentration crosses a threshold; and
   outputting onto a display an indication of whether the patient has SIBO based on the determination of whether the methane calibrated change in hydrogen gas concentration crosses the threshold.

2. The method of claim 1, wherein the step of determining a methane calibrated change in hydrogen gas concentration based on at least one of the first and second methane concentrations comprises increasing the change in hydrogen gas concentration by a factor proportional to at least one of the first and second methane gas concentrations.

3. The method of claim 1, wherein the step of determining a methane calibrated change in hydrogen gas concentration based on at least one of the first and second methane concentrations comprises determining whether the patient is a methane producer by determine whether at least one of the first and second methane concentrations crosses a second threshold and increasing the change in hydrogen gas concentration by a predetermine factor if the patient is determined to be a methane producer.

4. The method of claim 1, wherein the step of determining a methane calibrated change in hydrogen gas concentration based on at least one of the first and second methane concentrations comprises accessing a database of patient data correlated to known SIBO status and recorded hydrogen and methane concentrations.

5. The method of claim 4, wherein the database includes the ages of each subject.

6. A system for determining a likelihood of SIBO in patients, the system comprising:
   a breath collector;
   a testing chamber comprising a flow control device and a flow meter;
   a display;
   a hydrogen detector connected to the testing chamber configured to output hydrogen data representing a concentration of hydrogen in exhaled breath;
   a methane detector connected to the testing chamber configured to output methane data representing a concentration of methane in exhaled breath;
   a memory containing machine readable medium comprising machine executable code having stored thereon instructions for performing a method of a likelihood of the presence of MO in patients;
   at least one processor coupled to the memory, the at least one processor configured to execute the machine executable code to cause the at least one processor to:
      control a flow rate through the testing chamber using the flow control device based on feedback from the flow meter;
      determine, by the at least one processor, a first concentration of hydrogen gas based on a first set of hydrogen data detected by the hydrogen detector and a first concentration of methane gas based on a first set of methane data detected by the methane detector at a first time in breath exhaled from a patient before ingestion of a substance;

determine, by the at least one processor, a second concentration of hydrogen gas based on a second set of hydrogen data detected by the hydrogen detector and a second methane gas concentration based on a second set of methane data detected by the methane detector at a second time in breath exhaled from the patient after ingestion of the sub stance;

comparing the first and second hydrogen gas concentrations to determine a change in hydrogen gas concentration after ingesting the substance;

determining a methane calibrated change in hydrogen gas concentrations based on at least one of the first and second methane concentrations;

determining whether the methane calibrated change in hydrogen gas concentration crosses a threshold; and outputting onto the display an indication of whether the patient has SIBO based on the determination of whether the methane calibrated change in hydrogen gas concentration crosses the threshold.

7. The system of claim 6, wherein the at least one processor is further configured to send a notification to a clinician computing device of the indication of whether the patient has SIBO.

8. The system of claim 6, wherein determining the methane calibrated change further comprises reducing the change in hydrogen gas concentration by a predetermined amount if the patient is a methane producer.

9. The system of claim 6, wherein determining the methane calibrated change further comprises keeping the change in hydrogen gas concentration the same if the patient is not a methane producer.

10. The system of claim 6, wherein determining the methane calibrated change further comprises reducing the change in hydrogen gas concentration by a ratio correlated to at least one of the first and second methane concentrations.

* * * * *